US010485445B2

(12) United States Patent
Palikaras et al.

(10) Patent No.: US 10,485,445 B2
(45) Date of Patent: Nov. 26, 2019

(54) ELECTROMAGNETIC IMAGING

(71) Applicant: Medical Wireless Sensing Ltd, London (GB)

(72) Inventors: George Palikaras, London (GB); Efthymios Kallos, London (GB)

(73) Assignee: Medical Wireless Sensing Ltd, London (GB)

( * ) Notice: Subject to any disclaimer, the term of this patent is extended or adjusted under 35 U.S.C. 154(b) by 1180 days.

(21) Appl. No.: 14/389,293

(22) PCT Filed: Mar. 28, 2013

(86) PCT No.: PCT/GB2013/050841
§ 371 (c)(1),
(2) Date: Sep. 29, 2014

(87) PCT Pub. No.: WO2013/144652
PCT Pub. Date: Oct. 3, 2013

(65) Prior Publication Data
US 2015/0045663 A1 Feb. 12, 2015

Related U.S. Application Data

(60) Provisional application No. 61/617,968, filed on Mar. 30, 2012.

(30) Foreign Application Priority Data

Mar. 30, 2012 (GB) .................................. 1205798.0

(51) Int. Cl.
*A61B 5/05* (2006.01)
*A61B 5/00* (2006.01)
(Continued)

(52) U.S. Cl.
CPC .............. *A61B 5/0507* (2013.01); *A61B 3/14* (2013.01); *A61B 5/004* (2013.01); *A61B 5/0059* (2013.01);
(Continued)

(58) Field of Classification Search
CPC ............ G02B 1/002; A61B 2562/0228; A61B 2562/143; A61B 3/14; A61B 5/004;
(Continued)

(56) References Cited

U.S. PATENT DOCUMENTS 5,704,355 A * 1/1998 Bridges .................... A61B 5/05
600/407
6,621,370 B1 * 9/2003 Dao ........................ H03H 7/422
333/136
(Continued)

FOREIGN PATENT DOCUMENTS

CN 1700034 A 11/2005
DE 2736380 A1 2/1979
(Continued)

OTHER PUBLICATIONS

Notification of Transmittal of the International Search Report and the Written Opinion of the Internation Searching Authority, PCT/GB2013/050841, entitled "Electromagnetic Imaging," dated Jul. 17, 2013.
(Continued)

*Primary Examiner* — Mark D Remaly
(74) *Attorney, Agent, or Firm* — McDonnell Boehnen Hulbert & Berghoff LLP

(57) ABSTRACT

There is provided a device arranged to couple electromagnetic-imaging radiation from a source medium into an electromagnetic-imaging target, the device comprising a first supporting component having a thickness no greater than a wavelength of the electromagnetic-imaging radiation.
(Continued)

The first supporting component supports a planar array of first conducting elements, wherein each first conducting element has a first dimension no greater than a first wavelength of the electromagnetic-imaging radiation.

20 Claims, 9 Drawing Sheets

(51) Int. Cl.
*G02B 1/00* (2006.01)
*A61B 3/14* (2006.01)
*A61B 5/12* (2006.01)

(52) U.S. Cl.
CPC .............. *A61B 5/12* (2013.01); *A61B 5/4312* (2013.01); *A61B 5/6801* (2013.01); *G02B 1/002* (2013.01); *A61B 2562/0228* (2013.01); *A61B 2562/143* (2013.01)

(58) Field of Classification Search
CPC ....... A61B 5/0059; A61B 5/0507; A61B 5/12; A61B 5/4312; A61B 5/6801
See application file for complete search history.

(56) References Cited

U.S. PATENT DOCUMENTS

| | | | |
|---|---|---|---|
| 6,768,051 B2 * | 7/2004 | Wiltshire | H05K 9/0075 174/391 |
| 6,801,173 B2 * | 10/2004 | Wiltshire | H01Q 15/00 343/753 |
| 8,089,038 B1 | 1/2012 | Latypov | |
| 2004/0140945 A1 * | 7/2004 | Werner | H01Q 15/0086 343/909 |
| 2010/0078203 A1 | 4/2010 | Lier | |
| 2010/0271692 A1 | 10/2010 | Hor et al. | |
| 2010/0314040 A1 | 12/2010 | Tyler et al. | |
| 2011/0069377 A1 | 3/2011 | Wu et al. | |
| 2011/0287218 A1 * | 11/2011 | Narimanov | G02B 1/002 428/141 |
| 2011/0317275 A1 | 12/2011 | Smith | |
| 2012/0013989 A1 | 1/2012 | Choi et al. | |
| 2012/0015164 A1 | 1/2012 | Lin et al. | |
| 2012/0053445 A1 | 3/2012 | Turnquist | |
| 2012/0075692 A1 | 3/2012 | Baik | |
| 2012/0170114 A1 | 7/2012 | Domash | |
| 2012/0327502 A1 | 12/2012 | Zheludev et al. | |
| 2013/0240251 A1 | 9/2013 | Kaplan et al. | |
| 2014/0085693 A1 | 3/2014 | Mosallaei et al. | |
| 2015/0016030 A1 | 1/2015 | Browning et al. | |
| 2016/0361002 A1 | 12/2016 | Palikaras et al. | |

FOREIGN PATENT DOCUMENTS

| | | |
|---|---|---|
| EP | 0 694 282 A2 | 1/1996 |
| EP | 1860 458 A1 | 11/2007 |
| EP | 2 688 380 | 1/2017 |
| GB | 762734 | 12/1956 |
| GB | 2 382 230 A | 5/2003 |
| GB | 2 500 719 | 10/2013 |
| JP | 4002982 A | 11/2007 |
| RU | 2 089 166 C1 | 9/1997 |
| WO | WO 2005/053531 A2 | 6/2005 |
| WO | WO 2006/083672 A2 | 8/2006 |
| WO | WO 2012/007147 A1 | 1/2012 |
| WO | WO 2013/054115 A1 | 4/2013 |
| WO | WO 2013/144559 A1 | 10/2013 |

OTHER PUBLICATIONS

Great Britain Search Report, GB1205798.0, entitled "Device to couple electromagnetic imaging radiation from a source medium into an electromagnetic imaging target," date of search Jul. 30, 2012.

* cited by examiner

ELECTROMAGNETIC IMAGING

This application is the U.S. National Stage of International Application No. PCT/GB2013/050841, filed Mar. 28, 2013, which designates the U.S., published in English, which claims the benefit of U.S. Provisional Application No. 61/617,968, filed on Mar. 30, 2012, and claims priority under 35 U.S.C. §§ 119 or 365(c) to Great Britain Application No. 1205798.0, filed Mar. 30, 2012.

FIELD

The present disclosure relates to a device for coupling electromagnetic radiation into a target medium. In particular, the present disclosure relates to a device for increasing the penetration of electromagnetic radiation into a target medium. More particularly, the present disclosure relates to a wearable medium for medical imaging using non-ionising radiation, such as microwave medical imaging.

BACKGROUND

The World Health Organization (WHO) estimates 1.5 million new cases of breast cancer worldwide in 2010 with mortality exceeding 500,000, thus making breast cancer the leading cause for women deaths worldwide. The direct and indirect costs of breast cancer are staggering, with treatment costs approaching $8 billion annually and total costs, including treatment and losses in economic productivity amounting to $26 billion in 1996 (the latest year for which such information is available). According to Cancer Research UK (February 2011), a woman's risk of developing breast cancer has risen to one in eight over the last 10 years.

The most common imaging methods for cancer screening are Mammography and Magnetic Resonance Imaging (MRI). Other less frequently used methods include ultrasounds, positron emission tomography or thermology.

Currently, x-ray mammography is by far the incumbent technology for breast cancer screening. The process includes sandwiching the female breast between two plates, while low-energy ionizing X-rays are transmitted through the breast and imaged on a photographic plate. Women within the 'at-risk' age groups (between 49 and 70 years) are recommended to have regular screenings to enable early cancer detection. However a large number of patients are reluctant to undergo mammogram resulting in diagnosis at advanced stages of the disease. Detecting breast cancer at the advanced stages significantly reduces the effectiveness of medical intervention and life expectancy. Additionally delays lead to increased costs for both national and private health-service providers addressing breast cancer treatment.

The reluctance to avoid routine screenings has been identified to stem from the following issues with mammogram:

1) The use of ionising x-rays which pose a threat of causing (and increasing) cancer to patients in the course of repeated screenings leading to excessive exposure. The risk of radiation is higher among younger women due to their having higher breast tissue density, thus making current x-ray mammography devices potentially risky to this class of patients.
2) Negative user experience with existing equipment. The breast is pressed firmly between two plates, in order to obtain clear images from the X-ray. This process has been identified as a source of significant discomfort and pain to patients undertaking the procedure.

Research also shows there are significant risks of false diagnosis due to current the mammogram technique. There are two types of misdiagnosis:

1) False positive—this occurs when radiologists decide mammograms show abnormalities but no cancer is actually present. Natural News (2005) claimed that 70-80% of all positive mammograms do not, upon biopsy, show any presence of cancer. False-positive mammogram results can lead to anxiety and other forms of psychological distress in affected women. The additional testing required to rule out cancer can also be costly and time consuming and cause physical discomfort. Research (Brewer N T, et at 2007) shows that false-positive mammograms can significantly affect women's well-being and behaviour.
2) False negative—this occurs when mammograms appear normal even though breast cancer is present. According to National Cancer Institute (2010), screening mammograms miss up to 20 percent of breast cancers that are present at the time of screening.

Thermology derives diagnostic indications from detailed and sensitive infrared images of the human body. For breast cancer application, thermology has been primarily used for pre-cancer warning, but lacks credibility. The adoption rate for thermology was very slow and has only been deployed in a very limited number of clinics/health centres.

Ultrasound is cyclic sound pressure with a frequency greater than the upper limit of human hearing. The use of ultrasound technology in breast cancer screening is in an early stage and subject to further development.

In Magnetic Resonance Imaging (MRI), a breast is scanned in an MRI device before and after the intravascular injection of a contrast agent (Gadolinium DTPA). The pre-contrast images are "subtracted" from the post-contrast images, and any areas that have increased blood flow are seen as bright spots on a dark background. Since breast cancers generally have an increased blood supply, the contrast agent causes these lesions to "light up" on the images. The methods provides excellent resolution (around 1 mm) but it much more expensive and complicated to use compared to e.g. mammography.

Microwave medical imaging (MWI) is an emerging alternative to well established X-ray techniques as demonstrated by a growing body of research (see, for example, L. E. Larsen and J. H. Jacobi, Eds., Medical Applications of Microwave Imaging. Piscataway, N.J.: IEEE Press, 1986). For example, recent research has shown its potential as a low-cost way of detecting cancer, offering increased patient acceptability without the potential hazards of ionising radiation (see, for example, S. Semenov, "Microwave tomography: Review of the progress towards clinical applications," Phil. Trans. R. Soc. A, vol. 367, no. 1900, pp. 3021-3042, August 2009). In addition, non-invasive microwave-induced thermal therapy (hyperthermia) has also enjoyed significant progress over the last decade. Hyperthermia (40-45° C., typically for 60-90 min) causes direct cytotoxicity due to heat and increases sensitivity of cancer cells to radiation therapy and chemotherapy. As with most physics-based medical imaging and treatment methods, the clinical application and success of microwave-based techniques depends upon their ability to produce high-resolution imaging/focusing systems.

Microwave imaging operates via the principle of inverse scattering. An array of antennas is placed around the patient, focused towards the region of interest in the patient's human body. Due to the high permittivity and conductivity values of the tumour cells (which are typically much higher compared to the electromagnetic properties of the surrounding tissue), a significant portion of the wave energy will be scattered. This scattered energy is recorded and based on those signals the 3D image of the cancer cell region is reconstructed.

The imaging resolution of microwave imaging systems is compromised by the well-known Abbe-Rayleigh diffraction limit, which relates resolution to the illuminating wavelength of the imaging system. This is a critical issue for microwave systems, where typical wavelengths are of the order of centimetres. The imaging resolution is deteriorated by the reflection of the incident microwave radiation from the human tissue before reaching the tumour, and especially the skin. The microwave radiation has to transmit from outside the patient (e.g. air) through the skin and into the body. Since the skin has a relative dielectric permittivity around 50, a significant fraction of the incident energy is reflected and cannot by utilized to image the cancer regions. In electromagnetic terms, there is a large impedance mismatch between the air and the human body.

The present disclosure addresses some of these limitations. In particular, the present disclosure relates to improving the coupling of imaging radiation into a target medium.

SUMMARY

Aspects of the present disclosure are defined in the appended independent claims.

In summary, there is provided a device, such as a film, that can be placed right next to a target, such as a patient's skin surface, to improve the transmission of imaging waves into the target, thus addressing the image resolution problem and improving the accuracy of the overall imaging system. The device may used as a component of a complete medical imaging system.

Embodiments of the present disclosure may use non-ionising radiation such as microwave radiation. Such radiation is advantageous because it is safer than other types of radiation conventionally used for medical imaging of biological tissue, for example.

Advantageously, embodiments of the present disclosure provide an impedance matching medium which increases the amount of imaging radiation which enters the target medium. In examples, this is achieved by using at least one layer having a relative dielectric permittivity greater than a source medium (e.g. air) but less than that of the target medium (e.g. biological tissue). Accordingly, incident radiation encounters less of an impedance mismatch when travelling from a source medium to the target medium. The amount of radiation lost to reflect at the interface with the target medium is therefore reduced. Since more radiation enters the target, more of the incident radiation contributes to imaging. The resolution of the imaging system is therefore increased, and/or the system can be operated at a lower power level which would be enough to image the target. In an optional further improvement, a plurality of layers, such as dielectric layers or mediums, are positioned between the source and target, wherein each successive medium has a relative dielectric permittivity greater than the preceding medium but less than the subsequent medium. Accordingly, the impedance mismatch is further reduced.

The layer supports a planar array of first conducting elements, wherein each first conducting element has a first dimension no greater than a first wavelength of the imaging radiation. In this respect, the layer may be referred to as a supporting component. Such a component may also be referred to as a "metamaterial". The metamaterial may be arranged to resonant at a first wavelength of the imaging radiation to increase the penetration of radiation, at the first wavelength, into the target medium. In a yet further optional advancement, multiple metamaterial layers are positioned between the source and target, wherein each metamaterial is arranged to resonate at a different wavelength. Accordingly, an improved multiband system may be provided. In embodiments, the bands may at least partially overlap to provide a pseudo-broadband system.

In further improved embodiments, each conducting element may be coupled to a capacitor and/or inductor, such as a radio frequency capacitor and/or inductor, so that the resonant wavelength of the metamaterial may be electrically fine-tuned without physically replacing any of the elements. In embodiments, layers of metamaterials may be electrically connected.

The device in accordance with embodiments may be arranged to engage with existing medical imaging systems or may form a component of its own medical imaging system. Advantageous embodiments provide a wearable medium for a human target for medical imaging.

Imaging using electromagnetic waves or radiation is referred to herein as "electromagnetic imaging".

BRIEF DESCRIPTION OF THE DRAWINGS

Embodiments of the present disclosure will now be described with reference to the accompanying drawings in which.

In the figures, like reference numerals refer to like parts.

DETAILED DESCRIPTION OF THE DRAWINGS

Figure 1:
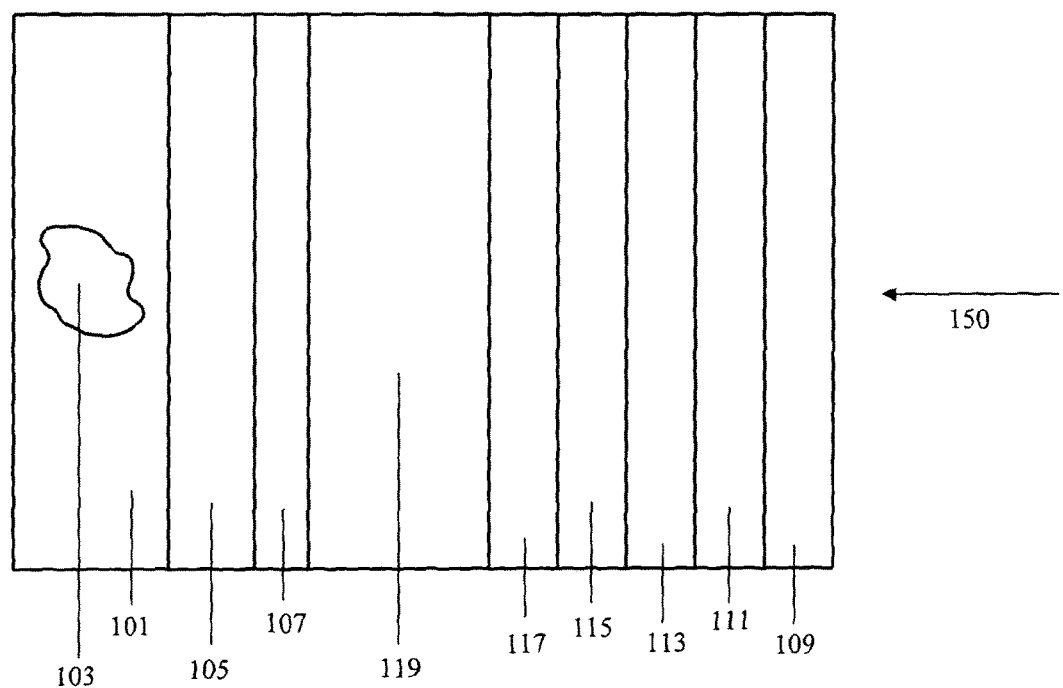
FIG. 1 is a schematic of a device in accordance with an example.

Embodiments disclosed herein refer to microwave radiation, and microwave imaging, by way of example only. The present disclosure is equally applicable to other types of electromagnetic imaging such as imaging using optical or visible wavelengths of radiation.

Embodiments disclosed herein also refer to the human body, and parts of the human body for medical imaging, by way of example only. The present disclosure is equally applicable to electromagnetic imaging of other targets including other types of biological tissue.

In overview, there is provided a device, such as a wearable medium, that enhances the penetration of non-ionizing microwave radiation inside the human body. The device can be used as a part of a microwave imaging system for cancer screening purposes, for example. In these systems, one or more antennas placed near a patient emit low-power radiation. A fraction of this radiation enters the human body and is scattered by the tumor which may lie inside. The scattered power is then received outside the body by the antennas. By properly processing the received signals, a three-dimensional image of the location and shape of cancer cells can be reconstructed. In embodiments, there is disclosed a film that applies directly to the surface of a patient, near the location of the body to be imaged, and enhances the penetration of the waves inside the body, thus increasing the accuracy and performance of the imaging system. Embodiments serve as an impedance matching medium.

Metamaterials are artificially created materials that can achieve electromagnetic properties that do not occur naturally, such as negative index of refraction or electromagnetic cloaking. While the theoretical properties of metamaterials were first described in the 1960s, in the past 10-15 years there have been significant developments in the design, engineering and fabrication of such materials. A metamaterial typically consists of a multitude of unit cells, i.e. multiple individual elements (sometimes refer to as "meta-atoms") that each has a size smaller, typically much smaller, than the wavelength of operation. It may be said that each element has at least one "sub-wavelength" dimension. These unit cells are microscopically built from conventional materials such as metals and dielectrics. However, their exact shape, geometry, size, orientation and arrangement can macroscopically affect radiation in an unconventional manner, such as creating resonances or unusual values for the macroscopic permittivity and permeability.

Some examples of available metamaterials are negative index metamaterials, chiral metamaterials, plasmonic metamaterials, photonic metamaterials, etc. Due to their sub wavelength nature, metamaterials that operate at microwave frequencies have a typical unit cell size of a few millimetres, while metamaterials operating at the visible part of the spectrum have a typical unit cell size of a few nanometres. Metamaterials can strongly absorb radiation at certain narrow range of frequencies.

For conventional materials, the electromagnetic parameters such as magnetic permeability and electric permittivity arise from the response of the atoms or molecules that make up the material to an electromagnetic wave being passed through. In the case of metamaterials, these electromagnetic properties are not determined at an atomic or molecular level. Instead these properties are determined by the selection and configuration of a collection of smaller objects, such as conducting components or elements, that make up the metamaterial. Although such a collection of objects and their structure do not "look" at an atomic level like a conventional material, a metamaterial can nonetheless be designed so that an electromagnetic wave will pass through as if it were passing through a conventional material. Furthermore, because the properties of the metamaterial can be determined from the composition and structure of such small objects, the electromagnetic properties of the metamaterial such as permittivity and permeability can be accurately tuned on a very small scale.

In embodiments, there is provided a film that applies to the skin surface and enhances the penetration of microwaves inside the human body. Broadly speaking, there is disclosed embodiments utilizing layers with a thickness less that the wavelength of the radiation of interest (i.e. sub-wavelength) and embodiments utilizing resonating metallodielectric metamaterials.

Dielectric Impedance Matching

A schematic of an example layer in accordance with the present disclosure, including sections of the human body, is shown in FIG. 1. An incident wave 150 is shown entering a plurality of dielectric layers 109, 111, 113, 115, 115. FIG. 1 shows five dielectric layers by way of example only and other examples comprise any number of layers, including just one layer. Next to the dielectric layers there is shown an optional disposable biocompatible layer 119, and then the human tissues start. A simple model of the human breast is shown in this example, consisting of a very thin skin layer 107, a fat layer 105, and then muscle 101. Other layers may exist after the muscle but are not shown here. The muscle layer 101 shown is a generic example of a tumour region 103 which has different electromagnetic properties than the rest of the tissue.

In more detail, FIG. 1 shows a section of human tissue comprising a layer of skin 107, followed by a layer of fat 105, followed by a layer of muscle 101, including a tumour 103. There is also shown a device in accordance with the present disclosure comprising five dielectric layers 109, 111, 113, 115, 117 and a disposable biocompatible layer 119 between the final dielectric layer 117 and the skin 107 of the target.

In an example, the dielectric layers consist of dielectric materials (either naturally occurring or composites), such as polymers or plastics. Their surface area extends over the area of the target that needs to be imaged. The individual layer thickness is sub-wavelength, and the number of layers can vary from one or a few (2-3) to dozens. The layers need not be of the same thickness. The exact individual layer thickness depends on the wavelength of radiation utilized in the system to probe the target, e.g. tumour tissue.

In examples, the dielectric is thermoplastic such as Plexiglass or Perspex. In other embodiments, the dielectric is polycarbonate, a composite (such as $SiO_2$ and a thermoplastic), glass or silica. However, other materials are equally suitable such as Teflon or a dielectric foam. Other examples use mixtures of materials, for example by loading polyurethane foam with high-permittivity barium titanate ($BaTiO_3$) inclusions.

There is therefore provided a device arranged to engage with an electromagnetic-imaging target to increase the penetration of electromagnetic-imaging radiation from a source medium into the target, the device comprising a first dielectric component having a thickness no greater than a wavelength of the electromagnetic-imaging radiation. In an example, a second dielectric component is arranged to receive electromagnetic-imaging radiation from the first dielectric component and transmit electromagnetic radiation towards the target. In a further example, at least a third dielectric component is arranged to receive electromagnetic radiation from an adjacent dielectric component, such as the second dielectric component, and transmit electromagnetic radiation towards the target. The thickness of each dielectric component may be no greater than a wavelength of the incident radiation.

Embodiments relate to microwave imaging in which the frequency of interest is 0.1 to 20 GHz. In examples, the thickness of the or each dielectric layer is 3 to 15 mm. In examples comprising a plurality of dielectric components, the total thickness of the device is 1.5 cm (one wavelength at 20 GHz) to circa 1 m (several wavelengths). In the latter example with a thick device, the device may be less portable and secured to the imaging apparatus which the patient approaches to position himself next to the apparatus. The relative dielectric permittivity of each dielectric component is 1-50.

Embodiments comprise an optional disposable component, such as a disposable layer. In embodiments, the disposable layer is "neutral", in the sense that it does not provide by itself any enhancement in the penetration. It is rather a separator between the dielectric layer/s and the target. In embodiments, the disposable layer is made from biocompatible materials, so that it can be disposed after the use by a patient. For subsequent use of the device, a new disposable layer is inserted, but the dielectric layer/s remain the same. In embodiments, the disposable material is soft and flexible in order to perfectly fill any gaps between the matching layer and the target. In other embodiments, the disposable layer provides some impedance matching or has a predetermined relative dielectric permittivity chosen to cooperate with the dielectric layer/s.

In one example, the device comprises 10 dielectric layers, each 1 cm thick. Their relative permittivities are equally distributed between 1 and 50, gradually increasing in value as the incident wave moves from source (e.g. air) towards the target (e.g. body). In an example, the relative dielectric permittivity distribution is [5, 10, 15, 20, 25, 30, 35, 40, 45, 50]. In another example, the distribution is [2, 3, 4, 5, 6, 7, 8, 9, 10, 11]. The skilled person will understand any number of layers may be used and any regularly or irregularly increasing distribution may be used. An operational principle here is that of adiabatic matching, wherein the wavelength of incident radiation does not perceive the individual features of the layers because the wave is much longer than the individual thicknesses of the layers. As the wave propagates towards increasingly higher permittivities, it does not suffer reflections because there is no abrupt change in the dielectric permittivity between the layers. In this way, the very high wave impedance of the human tissue, for example, is gradually matched to the impedance of free space. The wave does not suffer reflections because at no point does the impedance change abruptly.

The skilled person will understand how to select a dielectric material for each layer according to the required dielectric permittivity. In an example, the dielectric permittivity of each dielectric component may be controlled by using different loading densities of high permittivity powdered material such a barium titanate in a host material such as Teflon or a polymer-based material.

That is, in an example, the first dielectric component of the device has a relative dielectric permittivity greater than that of the source medium and less than that of the target. In an embodiment, there is provided a second dielectric component having a relative dielectric permittivity greater than that of the first dielectric component and less than that of the target. In a further example, there are provided further dielectric components wherein each dielectric component has a relative dielectric permittivity greater than that of an adjacent dielectric component and less than that of the target, and a subsequent layer, if there is one.

Metamaterial Components

In embodiments, the layer or layers of the above examples may be used as a supporting component, or supporting components, for additional components which collectively provide improved coupling of radiation into a target. An embodiment of the present disclosure—comprising the dielectric component, or components, of the above examples—further comprises a planar array of conducting components as shown in FIGS. 2 and 3.

Figure 2:
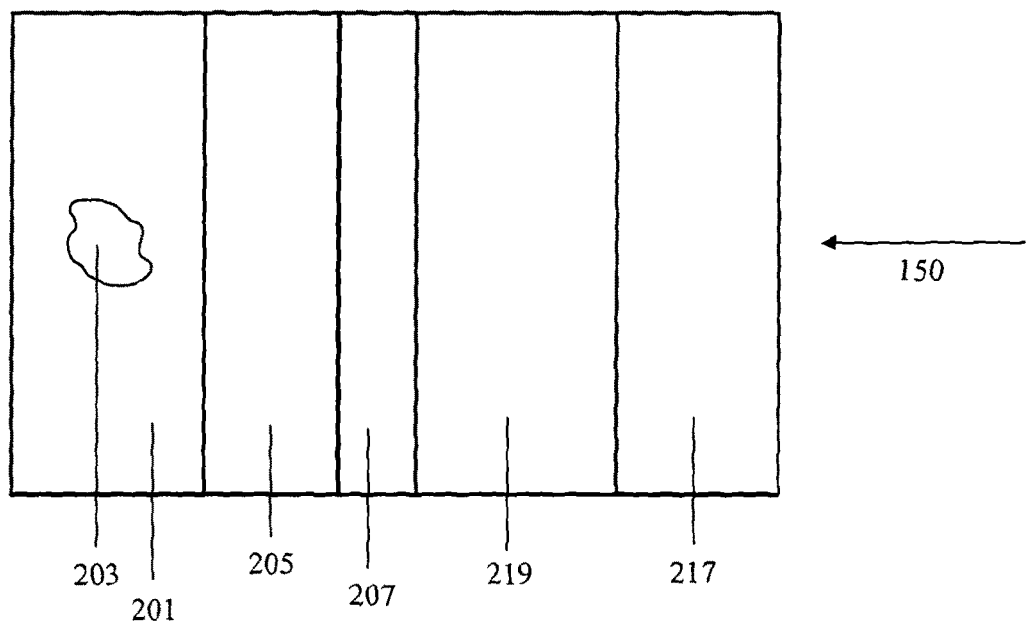
FIG. 2 is a schematic of an embodiment of the present disclosure.

FIG. 2 shows a target comprising a layer of skin 207, followed by a layer of fat 205, followed by a layer of muscle 201 including a tumour 203. The device in accordance with embodiments comprising a metamaterial component 217 and a disposable biocompatible layer 219 between the metamaterial component 217 and the skin 207 of the target.

Figure 3:
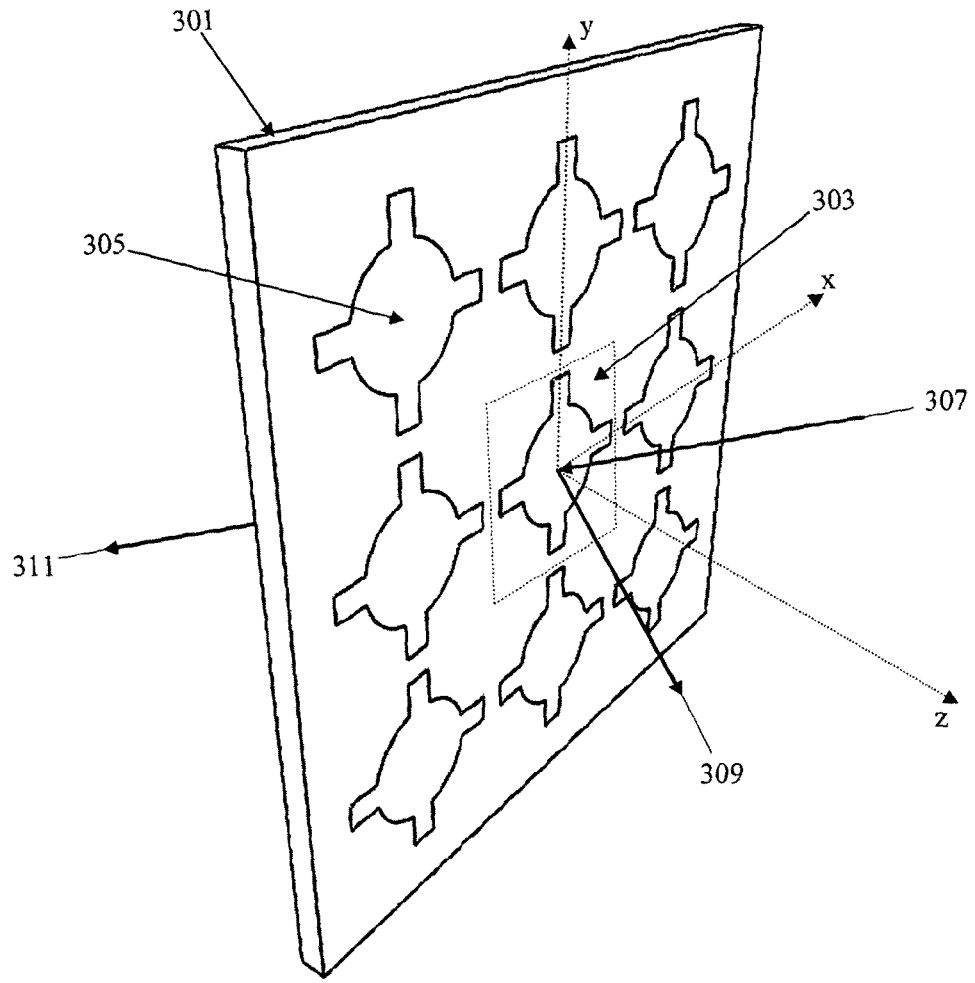
FIG. 3 shows a section of a metamaterial component in accordance with embodiments, the metamaterial component comprising a substrate/support material having periodic metallodielectric structures.

FIG. 3 shows an example dielectric component or substrate 301 supporting a planar array of unit cells 303 each comprising a conducting element 305, such as a metallic element. Such a material may be referred to as a metallo-dielectric material or metamaterial. FIG. 3 further shows an incidence wave 307, a reflected wave 309 and a transmitted wave 311. In other embodiments, the planer array of conducting components are supported by a material arranged to mimic internal biological tissue such as body fat and/or muscle. In these embodiments, the material may be said to mimic biological material by having a complex relative dielectric permittivity whose real and imaginary components are approximately equal to that of the biological material. This material may be referred to as a lossy dielectric or an imperfect dielectric. To reiterate, it can be understood that the component supporting the planar array of conducting components may be referred to as a supporting component.

There is therefore provided a device arranged to couple electromagnetic imaging radiation from a source medium into an electromagnetic imaging target, the device comprising a first supporting component having a thickness no greater than a wavelength of the electromagnetic-imaging radiation. The first supporting component supports a planar array of first conducting elements, wherein each first conducting element has a first dimension no greater than a first wavelength of the electromagnetic-imaging radiation.

In an embodiment, the first supporting component is a dielectric. In another embodiment, the first supporting element is a lossy dielectric or a material arranged to mimic internal biological tissue such as body fat and/or muscle. In an embodiment, the supporting material has a relative dielectric permittivity value which is between that of human body far and/or muscle and human skin. In an embodiment, the supporting material has a complex relative dielectric permittivity whose real and imaginary parts are approximately equal to that of internal body tissue such as body fat or body muscle but not skin.

The conducting component may be formed from any conducting material including homogeneous materials such as metals as well as composites and nanocomposites including Bragg reflectors. The conducting component may be formed, for example, from silver, gold, copper and/or aluminium, or any other metal that supports reflections at the wavelength of interest.

The thickness of the conducting component may be few micrometres to a few centimetres. Dimensions of the conducting component are sub-wavelength.

The skilled person will understand that any suitable technique for producing the conducting component on a supporting component, or support structure, may be appropriate. In embodiments, etching, photoresist etching, e-printing or lithographic techniques are used. In other embodiments, a self-assembly chemical process is used.

An operational principle of the metamaterial is that it is highly resonant around specific frequencies. For those frequencies, the wave transmission through the array is enhanced multiple times and thus increased wave penetration through the target occurs. The resonance condition is determined by the geometry of the array elements, and is optimized for transmission when it is placed on top of a particular target. That is, the components of the device are tailored to the target.

In embodiments, the planar array of first conducting elements are arranged to resonate at a first wavelength of the electromagnetic-imaging radiation.

Recent research on microwave artificial metallo-dielectric materials, or "metamaterials", has made significant advances in terms of demonstrating novel techniques for sub-wavelength focusing. According to this method, planar metallo-dielectric quasi-periodic surfaces can be used with appropriately modulated element dimensions in order to induce convergence of the near-field. These "near-field focusing structures" can lead to focusing details of size well below the diffraction limit. The use of these metallic structures is very promising in practical applications of imaging within dielectrics.

Figure 4:
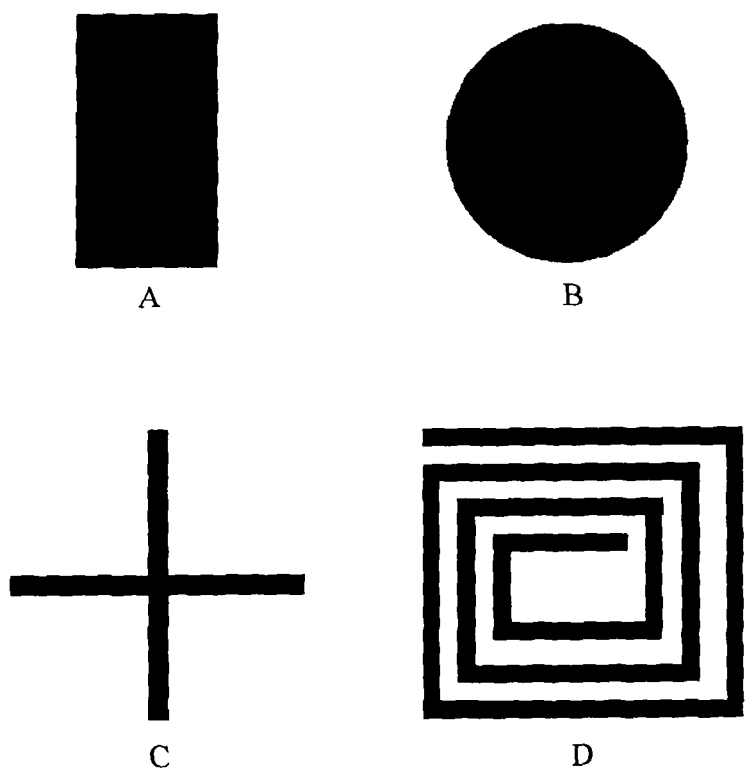
FIG. 4 shows some example possible shapes of conducting elements that can be used individually or combined to create a metamaterial unit cell in accordance with the present disclosure.

In embodiments, the conducting elements are metallic arranged in 2D periodic arrays of unit cells. These unit cells are arranged in a planar fashion and consist of a conducting component and a supporting component. Some example geometries for the conducting component are shown in FIG. 4. The conducting element may be, for example, a solid rectangle (FIG. 4A), a solid circle (FIG. 4B), a regular "+" shape (FIG. 4C), a right-angled meander (FIG. 4D) or a spiral. It may be noted that the unit cell include not only the main shape (e.g. rectangle or disk) but also the surrounding space. Each unit cell may comprise a combination of various geometries. In another embodiment, the different shapes are provided on different metamaterial layers. For example, a first layer may comprise a regular array of disks and a second layer may comprise a regular array of solid rectangles. In other embodiments, a plurality of shapes are included in each unit cell of a layer.

Figure 5:
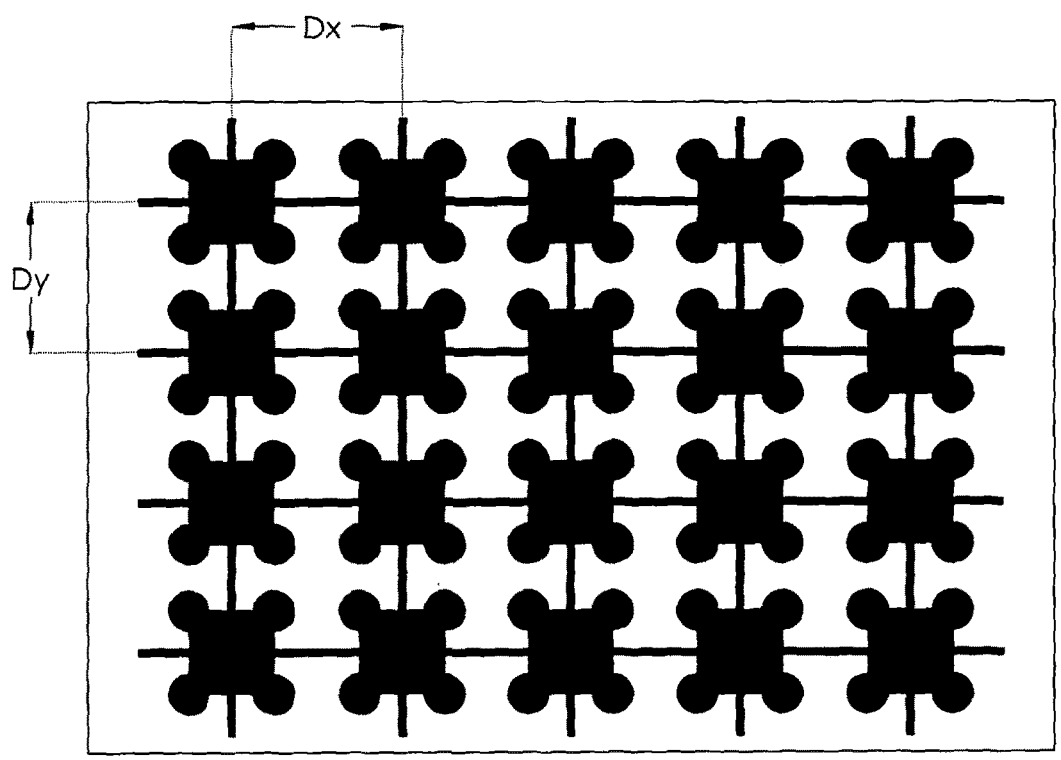
FIG. 5 shows a periodic array of metamaterial elements, which resonate (and provide transmission) at multiple bands, based on the geometrical shapes of the individual unit.

An example periodic array is further shown in FIG. 5. FIG. 5 shows an array comprising Nx by Ny elements placed at distances Dx and Dy with respect to each other. The overall thickness of the component (including the substrate) is typically microns or a few millimetres thick.

Either a single unit cell (such as the ones shown in FIG. 4) or a combination of them can comprise a unit cell. Each shape is arranged to resonant at a specific frequency or in specific frequency band (typically 5%-20% wide around the frequency of interest). In embodiments, multiple layers of metamaterials are combined together to provide resonance at multiple frequencies.

Figure 6:
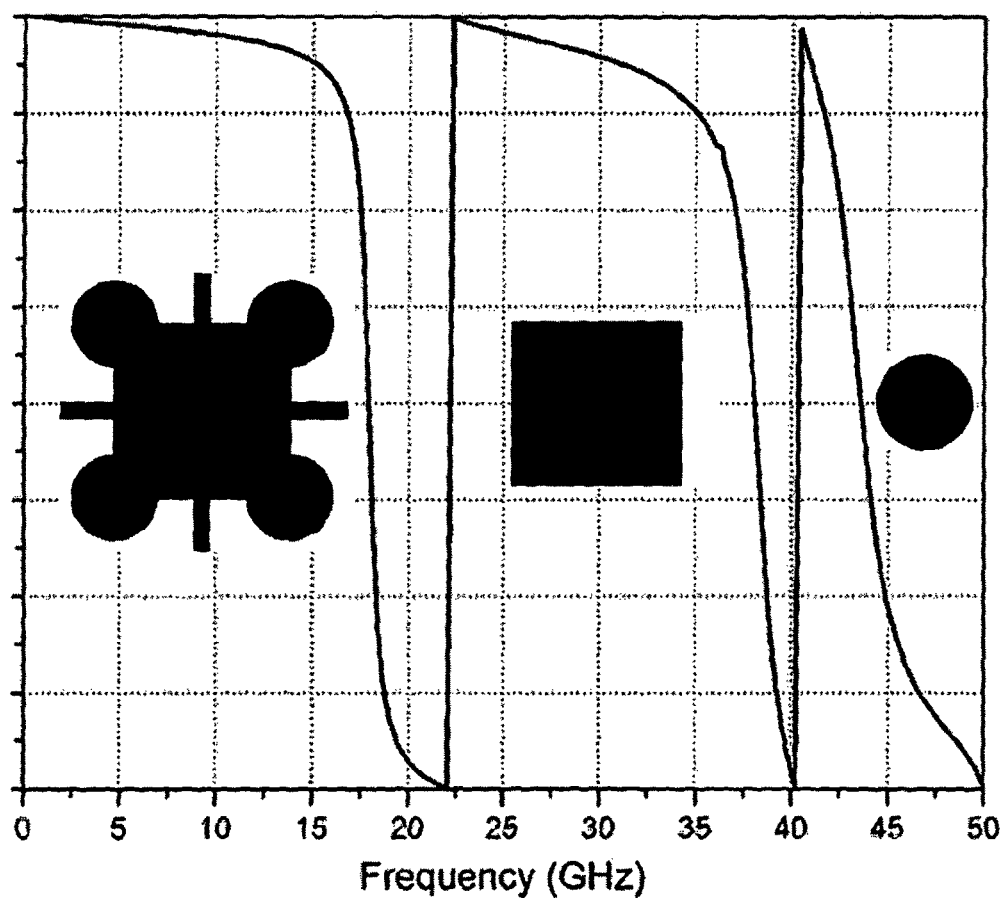
FIG. 6 shows that by combining different geometric shapes wherein each shape is tuned to resonate at a different frequency, multiple bands of resonance can be achieved.

The example in FIG. 5 shows a metamaterial unit element is composed of different simpler elements, and each element provides a resonance at a different frequency (see FIG. 6). In FIG. 6, the reflection off a periodic array of such elements is plotted, which is minimized at specific frequencies. Multiple elements can be used to optimize the penetration of different polarizations of incident microwaves, for example.

In embodiments relating to microwave imaging, the conducting components are separated by 6 to 50 mm.

Advantageously it is found that, when so arranged, the metamaterial in accordance with embodiments increases the intensity of radiation transmitted at a predetermined wavelength. This is owing to the ability to tune the unique properties of the metamaterial. Notably, the inventors have recognised that metamaterials, configured in accordance with the present disclosure, may be used to improve the resolution of medical imaging systems, for example, by increasing the penetration of radiation into the target.

The "sub-wavelength" periodic arrangement of metallic and dielectric elements allows the periodic conducing component to resonate at a resonant frequency (or wavelength). The skilled person will understand that there may be a narrow band of frequencies centred on the resonant frequency at which at least partial resonance will occur. At the resonant frequency, radiation will be at least partially "captured" by the metamaterial and amplification may occur by constructive interference, for example. The metamaterial forms a type of waveguide in which the fields inside the "waveguide" are bound and contained, permitting amplification. Accordingly, there is provided a device arranged to increase the penetration of radiation into a target.

In embodiments, the device is tuned to the source and target medium. It is found that an incident wave travels along the path of least resistance of the conducting component of the metamaterial. For example, if source provides a plane wave of radiation, symmetric conducting elements may be preferred. The shape and configuration of the conducting component may also be chosen to match the polarisation of the incident radiation. For example, conducting elements having horizontal and vertical features may be preferred for horizontally and vertically polarised radiation.

The conducting elements may comprise features having a length optimised for a wavelength of interest. In embodiments, the length of a primary feature is approximately half the wavelength of the incident radiation. For example, a conducting component having a long element, such as a spiral or a regular meander, will have a relatively long resonant wavelength. For example, the number of turns in the spiral of regular meander may be increased to increase the resonant wavelength. The conducting elements may comprise a sense of rotation such as a left-handed or right-handed spiral optimised for circularly or elliptically polarised radiation, for example. The shape and dimension of the elements may be optimised experimentally or numerically.

In embodiments, optimization of the shape of the elements is achieved via numerical simulation such that the device enhances the penetration of waves at a particular wavelength. In one embodiment, there is designed a model of the system in an electromagnetic simulator. The model includes all the components of the system: the source medium, the device component or components, the target medium, and any other features embedded in the target medium that needs to be imaged. Then the electromagnetic properties as a function of frequency of each component are specified, such as the electric permittivity, permeability, conductivity or loss. Then the S-parameters (reflection and transmission) of the system are evaluated as a function of frequency. The frequency range where the transmission is maximized indicated the optimal operational range of the system. When the geometry of the elements is modified, the transmission peak will be varied accordingly. Thus one can modify the shapes (or their period) to tune the operational frequency to the frequency or frequencies of interest (e.g. the radiation frequencies of the antenna system that generates the incident waves).

The device is tuned to the target medium. For example, the human body is frequency dispersive owing to the high water content. The frequency response of the target affects the behaviour of the device. Devices in accordance with the present invention are therefore tuned to the source, target and wavelengths of interest.

In an embodiment arranged to image a human female breast with vertically linearly polarised radiation at 400 MHz, the unit cell may comprise a rectangular conducting element made of copper having a length of 2 mm, a width of 1 mm and a thickness of 10 microns. The unit cells are arranged on a teflon substrate in a square array of 10×10 elements spaced by 5 mm in one direction (Dx) and 5 mm in the other perpendicular direction (Dy).

In another embodiment arranged to image a human arm with right-hand circularly polarized radiation at 1 GHz, the unit cell may comprise a spiral conducting element made of aluminium having a length of 10 mm, a width of 20 mm and a thickness of 20 microns. The unit cells are arranged on a glass substrate in a cylindrical array of 10×30 elements spaced by 25 mm in one direction (Dx—along the axis of the cylinder) and 15 mm in the other perpendicular direction (Dy—along the circular periphery of the cylinder). The embodiment can be fit around the arm.

The inventors have found that in order for the metamaterial to resonate, a minimum number of unit cells is required. Advantageously, the inventors have found that the metamaterial requires a length of at least 2.5λ in one dimension (wherein the unit cells are sub-wavelength).

The capacitance and inductance of the metamaterial device is determined by, at least, the dimensions of the conducting components including their thickness. The capacitive and inductive behaviour of the device may therefore be controlled by electrically connecting conducting components or layers of metamaterial, for example. Accordingly, the device may therefore be "tuned" to incident radiation at a particular wavelength. The skilled person will understand that the parameters of the layers may be altered accordingly to provide the desired electromagnetic response.

Embodiments disclosed herein refer to arrays of sub-wavelength conducing elements on a dielectric substrate by way of example only. In other embodiments, the dielectric material and conducting material may be interchanged. That is, the sub-wavelength elements may be dielectric and the substrate material may be conducting. In other embodiments, the supporting component is not a dielectric or is a lossy dielectric such as a material arranged to mimic internal biological tissue. In either configuration, there is provided a metamaterial comprising periodically arranged metallic elements.

In embodiments, the supporting component comprises a tissue mimicking material made by mixing a combination of raw materials such as gelatine, oil, propanol, toluic acid and distilled water in proper proportions.

The substrate, or supporting component, serves as a support structure for the shaped elements. In embodiments, the shaped elements are coated on the surface of the substrate. In other embodiments, the shaped elements are embedded within the substrate. The skilled person will understand that the array of shaped elements may be supported on the substrate in a variety of ways.

In embodiments, the device comprises a plurality of metamaterial layers. That is, a plurality of components or layers comprising periodically arranged metallic or dielectric elements having sub-wavelength features. Each metamaterial layer may be arranged to resonant at a different wavelength. In embodiments, by at least partially overlapping the resonant wavelengths of a plurality of metamaterials, a pseudo-broadband device is formed. For a pseudo-broadband device, the resonant frequency of adjacent layers may differ by an integer multiple of a half wavelength, for example.

That is, in an embodiment, there is provided a second supporting component supporting a planar array of second conducting elements wherein each second conducting element has a first dimension no greater than a second wavelength of the electromagnetic-imaging radiation. In an embodiment, the planar array of second conducting elements are arranged, in cooperation with the first supporting component, to resonate at the second wavelength of the electromagnetic-imaging radiation, wherein the second wavelength is different to the first wavelength of the first metamaterial.

In embodiments, there is provided a disposable biocompatible layer arranged to couple the device to the target. In embodiments, the disposable biocompatible layer may be provided for reasons of hygiene. In other embodiments, the disposable biocompatible layer may comprise a dielectric component, optionally, supporting a planar array of conducting elements. The disposable biocompatible layer may therefore be "tuned" to the rest of the device. The disposable biocompatible layer may be deformable and/or may have a morphology arranged to attach to a part of the human body. The disposable biocompatible layer may be formed from a polymer-based material.

Figure 7:
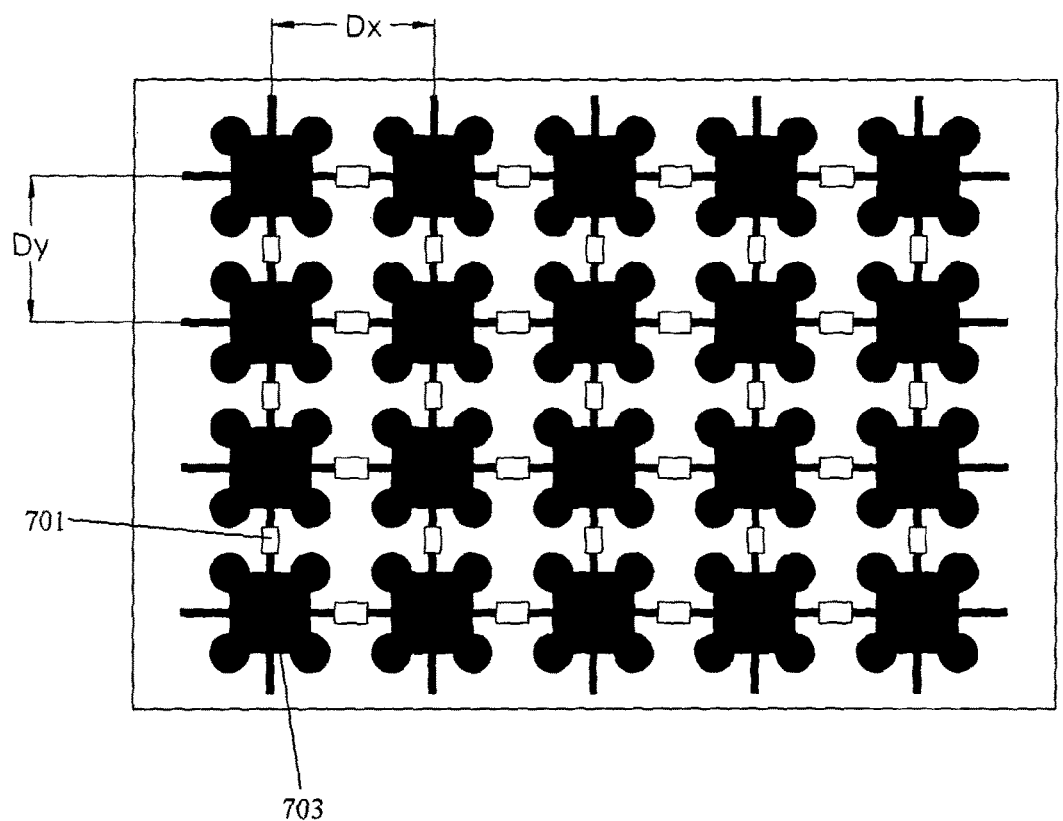
FIG. 7 shows a periodic metamaterial array loaded with radio frequency capacitors and inductors wherein by tuning the values of the capacitors/inductors, the bands of operation (transmission) of the array can be fine-tuned.

In embodiments, the frequencies of operation of the device can be made tunable on demand by adding radio frequency capacitors and/or inductors 701 connected to the metamaterial elements 703, as shown in FIG. 7. At least two of the first conducting elements may be electrically connected, optionally, by radio frequency capacitors and/or inductors. These may be standard RF components that can be easily printed and connected to the metallic elements. Their capacitance and inductance values are determined electronically through an external controller (not shown). The skilled person will understand that by changing these values, the resonance frequencies may be tuned accordingly. In embodiments, the device may be actively tuned. At least one of the first conducing elements may be electrically connected to a radio frequency capacitor and/or insulator.

Figure 8:
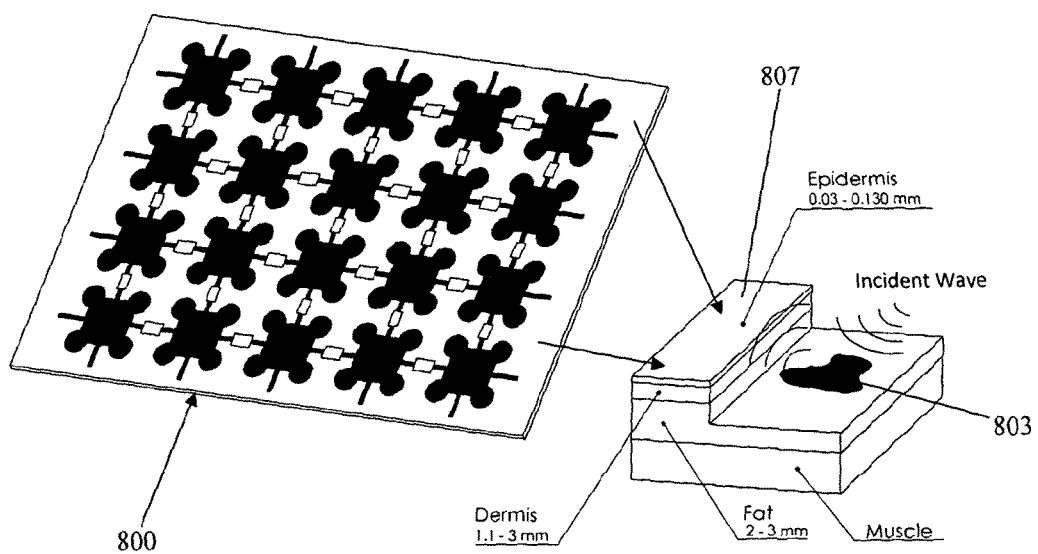
FIG. 8 is a schematic showing an application of embodiments onto a skin surface including a tumour inside the tissue.

FIG. 8 shows an example of how a planar metamaterial array 800 can be placed on top of the skin 807 to image a tumour 803 inside the tissue.

Figure 9:
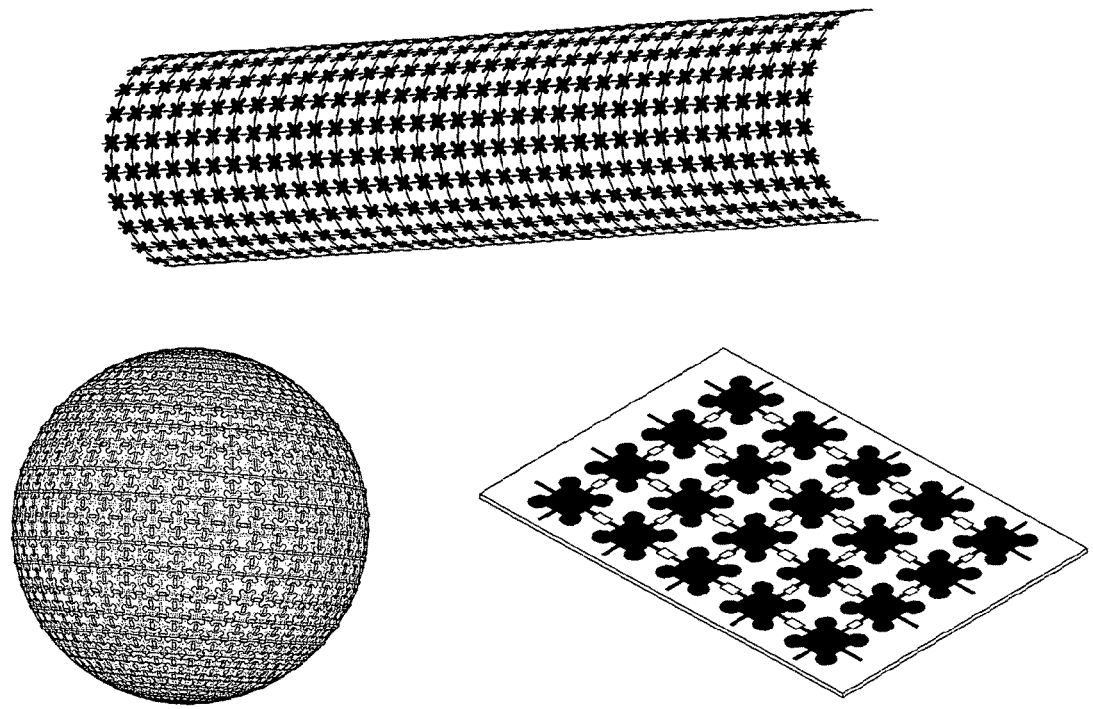
FIG. 9 shows three different configurations for the arrangement of the periodic array planar, cylindrical, spherical (curved)—wherein the cylinder and sphere may come in different sizes, to fit around different parts of the body and different body sizes.

FIG. 9 shows three embodiments comprising different possible geometrical arrangements of the metamaterial elements: planar, cylindrical, and spherical. In other embodiments, the arrangement is a section of a sphere or cylinder. The different shapes may be arranged so that the device can be fit around different parts of the human body, such as the breast, a leg, the neck, the waist, the arm, an ear etc. In embodiments, the device may therefore be wearable, coming into direct contact with the skin. In embodiments especially for breast imaging, the device may be made to have the shape of a brassiere for exact fitting. Embodiments may be used for the imaging of cancerous or non-cancerous regions of the human body such as broken bones.

In embodiments, microwave imaging is used for the imaging of biological material, such as a human breast. In other embodiments, optical wavelengths may be used to image a human eye. In further embodiments, the target is an ear or a section of an ear.

Advantageously, the device in accordance with embodiments of the present disclosure is passive. That is, it does not require a power supply. The device may therefore increase the overall energy efficiency of a medical imaging system The device may be arranged in cooperation with, such as in between, a source and detector to form an electromagnetic-imaging system. The system may further comprise processing means arranged to receive date from the detector and detect areas of relative high dielectric permittivity within the target.

Although aspects and embodiments have been described above, variations can be made without departing from the inventive concepts disclosed herein.

The invention claimed is:

1. An electromagnetic-imaging system comprising:
a source of electromagnetic radiation arranged to irradiate a target, wherein the electromagnetic radiation travels from a source medium to the target, wherein the source medium is air;
a detector arranged to detect radiation emitted from the target; and
a device, arranged between the source medium and the target, the device comprising a first supporting component having a thickness no greater than a first wavelength of the electromagnetic radiation, wherein the first supporting component supports a planar array of first conducting elements, wherein each first conducting element has a dimension no greater than the first wavelength of the electromagnetic radiation, wherein the first supporting component has a relative dielectric permittivity greater than that of the source medium and less than that of the target.

2. An electromagnetic-imaging system as claimed in claim 1, further comprising a processor arranged to process data received from the detector and detect the presence of areas of higher dielectric permittivity within the target.

3. An electromagnetic-imaging system as claimed in claim 1, wherein the first supporting component is formed from material comprising at least one selected from the group comprising a dielectric; a lossy dielectric; and a material having a complex relative dielectric permittivity having a real and imaginary component approximately equal to internal biological tissue.

4. An electromagnetic-imaging system as claimed in claim 1, wherein the planar array of first conducting elements is arranged to resonate at the first wavelength of the electromagnetic radiation.

5. An electromagnetic-imaging system as claimed in claim 1, wherein the at least one of the first conducting elements is electrically connected to a radio frequency capacitor and/or inductor.

6. An electromagnetic-imaging system as claimed in claim 1, wherein the device further comprises a second supporting component arranged to receive electromagnetic radiation from the first supporting component and transmit electromagnetic radiation towards the target.

7. An electromagnetic-imaging system as claimed in claim 6, wherein the second supporting component has a thickness no greater than a wavelength of the electromagnetic radiation.

8. An electromagnetic-imaging system as claimed in claim 6, wherein the second supporting component has a relative dielectric permittivity greater than that of the first dielectric component and less than that of the target.

9. An electromagnetic-imaging system as claimed in claim 6, wherein the second supporting component supports a planar array of second conducting elements wherein each second conducting element has a first dimension no greater than a second wavelength of the electromagnetic radiation.

10. An electromagnetic-imaging system as claimed in claim 9, wherein the planar array of second conducting elements are arranged, in cooperation with the first supporting component, to resonate at the second wavelength of the electromagnetic radiation.

11. An electromagnetic-imaging system as claimed in claim 10, wherein the resonant wavelength of the planar array of second conducting elements is different to the resonant wavelength of the planar array of first conducting elements.

12. An electromagnetic-imaging system as claimed in claim 6, wherein the device further comprises at least a third supporting component, arranged to receive electromagnetic radiation from an adjacent supporting component and transmit electromagnetic radiation towards the target.

13. An electromagnetic-imaging system as claimed in claim 12, wherein each supporting component has a thickness no greater than a wavelength of the electromagnetic radiation.

14. An electromagnetic-imaging system as claimed in claim 12, wherein each supporting component has a relative dielectric permittivity greater than that of an adjacent supporting component and less than that of the target.

15. An electromagnetic-imaging system as claimed in claim 12, wherein each of the supporting components supports a planar array of conducting elements, wherein each conducting element has a first dimension no greater than a wavelength of the electromagnetic radiation and is arranged to resonate at a wavelength of the electromagnetic radiation.

16. An electromagnetic-imaging system as claimed in claim 1, wherein the device further comprises a disposable biocompatible layer arranged to couple the device to the target.

17. An electromagnetic-imaging system as claimed in claim 16, wherein the disposable biocompatible layer comprises a dielectric component supporting a planar array of conducting elements.

18. An electromagnetic-imaging system as claimed in claim 1, wherein the target comprises biological tissue or wherein the target is a section of the human body.

19. An electromagnetic-imaging system as claimed in claim 18, wherein the section of human body is an eye, breast or ear.

20. An electromagnetic-imaging system as claimed in claim 1, wherein the device is wearable and/or wherein the device is passive.

* * * * *